United States Patent [19]

Elliott et al.

[11] Patent Number: 4,902,332
[45] Date of Patent: Feb. 20, 1990

[54] PYRIMIDINE DERIVATIVES

[75] Inventors: Raymond Elliott; Brian K. Snell, both of Reading; Raymond S. Gairns, Whitefield, all of England

[73] Assignee: Imperial Chemical Industries PLC, London, United Kingdom

[21] Appl. No.: 234,651

[22] Filed: Aug. 22, 1988

[30] Foreign Application Priority Data

Aug. 20, 1987 [GB] United Kingdom ............... 8719694
Dec. 18, 1987 [GB] United Kingdom ............... 8729583

[51] Int. Cl.⁴ .................. A01N 43/40; A61K 31/505; C07D 239/26
[52] U.S. Cl. .......................................... 71/76; 71/92; 514/269; 544/335
[58] Field of Search ............... 544/335; 514/269; 71/76, 92

[56] References Cited

U.S. PATENT DOCUMENTS 4,713,456 12/1987 Elbe et al. ................... 544/335
4,806,644 2/1989 Elbe et al. ................... 544/335

FOREIGN PATENT DOCUMENTS 1218623 4/1968 United Kingdom .
1468840 3/1977 United Kingdom .

Primary Examiner—Glennon H. Hollrah
Assistant Examiner—James H. Turnipseed
Attorney, Agent, or Firm—Cushman, Darby & Cushman

[57] ABSTRACT

Pyrimidine derivatives useful as plant growth regulators and fungicides having the general formula (I):

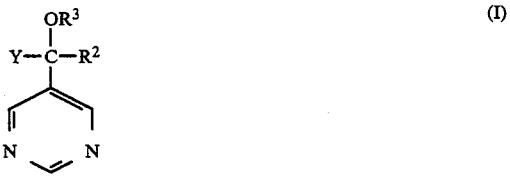

wherein Y is optionally substituted cyclopropyl or 1-methyl-cyclopropyl or is optionally halo-substituted isopropyl or t-butyl; $R^2$ is a group;

$-(CH_2)_m-C\equiv C-A$ or $-(CH_2)_n-CH=CH-A$ or $-(CH_2)_p-A$ wherein A is an optionally substituted phenyl group, m and n are integers from 0 to 2 and p is an integer from 2 to 4; and $R^3$ is hydrogen or lower alkyl or alkenyl or alkynyl containing from 3 to 4 carbon atoms.

9 Claims, No Drawings

PYRIMIDINE DERIVATIVES

PYRIMIDINE DERIVATIVES

This invention relates to pyrimidine derivatives useful as plant growth regulating agents and fungicides, to processes for preparing them, to compositions containing them and to methods of regulating plant growth and combatting fungal diseases in plants using them.

According to the present invention there is provided a pyrimidine derivative having the general formula (I):

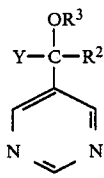
(I)

and stereoisomers thereof, wherein Y is optionally substituted cyclopropyl or optionally substituted 1-methylcyclopropyl or is the group:

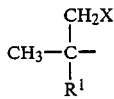
(II)

wherein $R^1$ is hydrogen or methyl; X is hydrogen or halogen; $R^2$ is a group:

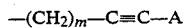 (III)

or

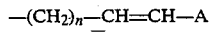 (IV)

or

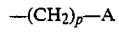 (V)

wherein A is an optionally substituted phenyl group, m is an integer from 0 to 2, n is an integer from 0 to 2 and p is an integer from 2 to 4; and $R^3$ is hydrogen, an alkyl group containing from 1 to 4 carbon atoms, an alkenyl group containing from 3 to 4 carbon atoms or an alkynyl group containing from 3 to 4 carbon atoms and agrochemically acceptable salts, esters and metal complexes of the compounds of the formula (I) wherein $R^3$ is hydrogen.

The compounds of the invention contain one or more chiral centres. Such compounds are generally obtained in the form of racemic mixtures. However, these and other mixtures can be separated into the individual isomers by methods known in the art, and this invention embraces such isomers.

Where X is halogen, it is preferably chlorine or fluorine.

Optional substituents which may be present in the group Y include lower alkyl (for example $C_1$ to $C_4$ alkyl) and halogen, especially monohalogen, for example chlorine or fluorine.

As examples of optional substituents which may be present in the phenyl group, A, there may be mentioned one or more substituents selected from halogen, for example chlorine or fluorine; alkyl (for example lower alkyl); cycloalkyl (for example cycloalkyl containing from 3 to 6 carbon atoms); alkoxy, for example lower alkoxy; haloalkyl, for example lower haloalkyl; lower alkoxy carbonyl (for example $-COOCH_3$); lower alkyl carbonyl (for example $-CO.CH_3$); nitro; and cyano. The term "lower" as applied to the above groups indicates that the group contains from 1 to 6, and preferably from 1 to 4 carbon atoms.

Thus as specific examples of the group A there may be mentioned phenyl, o-, m- and p-chlorophenyl; o-, m- and p-fluorophenyl; dichlorophenyl (for example 2,4-dichlorophenyl); difluorophenyl (for example 2,4-difluorophenyl); o-, m- and p-methylphenyl; o-, m- and p-trifluoromethylphenyl; o-, m- and p-methoxyphenyl; chlorofluorophenyl (for example 3-chloro-4-fluoro); o-, m- and p-methoxyphenyl; and o-, m- and p-nitrophenyl.

Preferred groups $R^3$ are hydrogen and methyl. Hydrogen is especially preferred.

The integers n and m are preferably 0. The integer p is preferably 2.

The present invention includes salts, esters and metal complexes of the compounds of formula (I) wherein $R^3$ is hydrogen. As examples of esters (acylates) there may be mentioned for example acetates or benzoates. As examples of salts there may be mentioned for example toluene sulphonate salts, dodecylbenzene sulphonate salts, hydrochloride salts, hydrobromide salts and orthophosphate salts. Without limitation of the generality of the above statement, the present invention also includes any compound which breaks down in agrochemical use to a compound of formula (I).

Examples of the compounds of the invention are presented in Table I in which the values for $R^1$, $R^2$, $R^3$ and X in the general formulas (I) and (II) above are as indicated.

In Table I, the phenyl group is represented by -phenyl.

TABLE I

| COMPOUND NO. | $R^1$ | $R^2$ | $R^3$ | X | MELTING POINT (°C.) | COMMENTS |
|---|---|---|---|---|---|---|
| 1 | H | $-C\equiv C-$phenyl | H | H | 112–113 | |
| 2 | H | $-CH_2-CH_2-$phenyl | H | H | gum | |
| 3 | $CH_3$ | $-C\equiv C-$phenyl | H | H | 118 | |
| 4 | $CH_3$ | $-CH_2-CH_2-$phenyl | H | H | 95–97 | |
| 5 | H | $-C\equiv C-$(4-chlorophenyl) | H | H | 113.5–115 | |
| 6 | $CH_3$ | $-CH_2-CH_2-$(4-chlorophenyl) | H | H | 154–156 | |
| 7 | $CH_3$ | $-CH_2-CH_2-$(4-methoxyphenyl) | H | H | 98.5–99.5 | |
| 8 | $CH_3$ | $-CH_2-CH_2-$(2,4-dichlorophenyl) | H | H | 144.5–147 | |
| 9 | H | $-C\equiv C-$(4-methylphenyl) | H | H | 113–115 | |
| 10 | H | $-C\equiv C-$(4-methoxyphenyl) | H | H | 99–101 | |
| 11 | H | $-C\equiv C-$(2-chloro-4-fluorophenyl) | H | H | 91–94 | |
| 12 | H | $-CH=CH-$(2,4-dichlorophenyl) | H | H | 111–113 | trans isomer |
| 13 | H | $-CH=CH-$(4-fluorophenyl) | H | H | 118.5–122 | trans isomer |
| 14 | H | $-CH=CH-$(2-methoxyphenyl) | H | H | Oil | trans isomer |

TABLE I-continued

| COMPOUND NO. | $R^1$ | $R^2$ | $R^3$ | X | MELTING POINT (°C.) | COMMENTS |
|---|---|---|---|---|---|---|
| 15 | H | —≡CH—(4-methylphenyl) | H | H | 124–127 | trans isomer |
| 16 | H | —CH≡CH—(4-methylphenyl) | H | H | 157–159 | trans isomer |
| 17 | H | —CH≡CH—(4-chlorophenyl) | H | H | 153–155.5 | trans isomer |
| 18 | H | —C≡CH—4-fluorophenyl) | H | H | 95–96 | |
| 19 | H | —C≡C—(2,4-difluorophenyl) | H | H | 92–93 | |

Compounds of general formula (I) above wherein $R^3$ is hydrogen and Y is as defined may be prepared by reacting a compound of general formula (II):

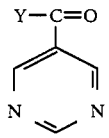
(VI)

with an organometallic compound which may be represented by the general formula (VII):

$R^2M$          (VII)

where M is a suitable metal, for example lithium, magnesium, titanium or zirconium.

The reaction conveniently takes place in a solvent such as diethylether, tetrahydrofuran or dichloromethane at −80° C. to +80° C. in an inert atmosphere. The product is obtained by quenching with a proton donor. When M is magnesium, the organometallic compound is more specifically $R^2$-Mg-halogen. When M is titanium, the organometallic compound is more specifically $R^2$-Ti(O alkyl)$_3$. When M is zirconium, the organometallic compound is more specifically $R^2$-Zr(O alkyl)$_3$.

The compounds of general formula (I) wherein $R^3$ is hydrogen may also be prepared by reacting a ketone of general formula (VIII), wherein Y and $R^2$ are as defined with an organometallic compound which may be represented by the general formula (IX) wherein M is a suitable metal, for example lithium:

(VIII)

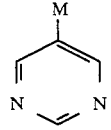
(IX)

The reaction preferably takes place in a suitable solvent such as diethyl ether or tetrahydrofuran at a temperature of from −120° C. to +80° C. and in an inert atmosphere. The product is obtained by quenching with a suitable proton donor.

The ketones of general formula (VI) and (VIII) may be prepared using standard methods set out in the literature.

Olefinic alcohols wherein $R^2$ is the group —CH=CH—A wherein A is as defined above may be made by the reduction of the corresponding acetylenic alcohol wherein $R^2$ is —C≡C—A. Suitable reducing agents include hydrogen in the presence of a suitable catalyst such as palladium on a support such as carbon (for example a Lindlar catalyst); or a metal hydride reducing agent such as lithium aluminium hydride, "Red-Al" (sodium bis [2-methoxyethoxy] aluminium hydride) or sodium borohydride/palladium (II) chloride in a suitable solvent such as ether or tetrahydrofuran.

Similarly, compounds of formula (I) wherein $R^2$ is a group:

—CH$_2$CH$_2$—A where A is as defined above, may be made by the complete reduction of the corresponding acetylenic alcohol, —C≡C—A. Suitable reducing agent as palladium, platinum or rhodium on a support such as carbon and in a suitable solvent such as methanol, ethanol or acetic acid.

The ethers (wherein $R^3$ is alkyl) and esters of the invention may be made from the corresponding hydroxy compound by reaction with the appropriate halide, acid chloride or acid anhydride in the presence of a suitable base.

The plant growth regulating effects of the compounds are manifested as, for example, by a stunting or dwarfing effect on the vegetative growth of woody and herbaceous mono- and di-cotyledonous plants. Such stunting or dwarfing may be useful, for example, in peanuts, cereals such as wheat and barley, oil seed rape, field beans, sunflowers, potatoes and soya bean where reduction in stem height, with or without further advantageous effects such as stem strengthening, thickening and shortening, internode shortening, increased buttress root formation and more erect stem and leaf orientation, may reduce the risk of lodging and may also permit increased amounts of fertiliser to be applied. The stunting of woody species is useful in controlling the growth of undergrowth under power lines etc. Compounds which induce stunting or dwarfing may also be useful in modifying the stem growth of sugar cane thereby increasing the concentration of sugar in the cane at harvest; in sugar cane, the flowering and ripening may be controllable by applying the compounds. Stunting of peanuts can assist in harvesting. Growth retardation of grasses can help maintenance of grass swards. Examples of suitable grasses are *Stenotaphrum secundatum* (St. Augustine grass), *Cynosurus cristatus, Lolium multiflorum* and *perenne, Agrostis tenuis, Cynodon dactylon* (Bermuda grass), *Dactylis glomerata, Festuca* spp. (e.g., *Festuca rubra*) and *Poa* spp. (e.g., *Poa pratense*). The compounds may stunt grasses without significant phytotoxic effects and without deleteriously affecting the appearance (particularly the colour) of the grass; this makes such compounds attractive for use on ornamental lawns and on grass verges. They may also have an effect on flower head emergence in, for example, grasses. The compounds can also stunt weed species present in the grasses; examples of such weed species are sedges (e.g., *Cyperus* spp.) and dicotyledonous weeds (e.g., daisy, plantain, knotweed, speedwell, thistle, docks and ragwort). The growth of non-crop vegetation (e.g., weeds or cover vegetation) can be retarded thus assisting in the maintenance of plantation and field crops. In fruit orchards, particularly orchards subject to soil erosion, the presence of grass cover is important. However excessive grass growth requires substantial maintenance. The compounds of the invention could be useful in this situation as they could restrict growth without killing the plants which would lead to soil erosion; at the same time the degree of competition for nutrients and water by the grass would be reduced and this could result in an increased yield of fruit. In some cases, one grass species may be stunted more than another grass species; this selectivity could be useful, for example, for improving the quality of a sward by preferential suppression of the growth of undesirable species.

The dwarfing may also be useful in miniaturising ornamental, household, garden and nursery plants (e.g., poinsettias, chrysanthemums, carnations, tulips and daffodils).

As indicated above, the compounds can also be used to stunt woody species. This property can be used to control hedgerows or to shape or reduce the need for pruning, of fruit trees (e.g., apples, pears, cherries, peaches, vines etc).

The plant growth regulating effect may (as implied above) manifest itself in an increase in crop yield; or in an ability in orchards and other crops to increase fruit set, pod set and grain set. Some coniferous trees are not significantly stunted by the compounds so the compounds could be useful in controlling undesirable vegetation in conifer nurseries.

In the potato, vine control in the field and inhibition of sprouting in the store may be possible.

In addition the compounds may be useful as absicision agents resulting in thinning of fruit on the tree and an increase in fruit quality.

Other plant growth regulating effects caused by the compounds include alteration of leaf angle and changes in leaf morphology (both of which may permit increased light interception and utilization) and promotion of tillering in monocotyledonous plants. Improved light interception is of value in all major world crops, e.g., wheat, barley, rice, maize, soya, sugarbeet, potatoes, plantation crops and orchard crops. The leaf angle effect may be useful for example in altering the leaf orientation of, for example, potato crops thereby letting more light into the crops and inducing an increase in photosynthesis and tuber weight. By increasing tillering in monocotyledonous crops (e.g., rice), the number of flowering shoots per unit area may be increased thereby increasing the overall grain yield of such crops. In addition better control and modification of hierarchical relationships is possible both in vegetative and reproductive stages of monocotyledonous and dicotyledenous plant growth, especially in cereals such as wheat, barley, rice and maize, whereby the number of flowering shoots per unit area may be increased and the size distribution of grains within the ear may be modified in such a way as to increase yield. In the treatment of rice plants, or rice crops the invention compounds can be applied, e.g., as granules or a granular formulation, for example as slow release granules, to nursery boxes, paddy water and other like cultivation loci and media. In grass swards, especially amenity grass, an increase in tillering could lead to a denser sward which may result in increased resilience in wear; and to increased yields and better quality of forage grass, e.g., improved digestability and palatability.

The treatment of plants with the compounds can lead to the leaves developing a darker green colour. In dicotyledonous plants such as soyabean and cotton, there may be promotion of sideshooting.

The compounds may inhibit, or at least delay, the flowering of sugar beet (and thereby may increase sugar yield) or otherwise modify the flowering patterns in many other crops. They may also reduce the size of sugar beet without reducing significantly the sugar yield thereby enabling an increase in planting density to be made. Similarly in other root crops (e.g., turnip, swede, mangold, parsnip, beetroot, yam and cassava) it may be possible to increase the planting density.

The compounds could be useful in restricting the vegetative growth of cotton thereby leading to an increase in cotton yield. Crop yields may also be increased by improvement of the harvest index (i.e. the harvested yield as a proportion of the total dry matter produced) by altering dry matter partitioning. This applies to all the aforementioned root, pod, cereal, tree, plantation and orchard crops.

The compounds may be useful in rendering plants resistant to stress since the compounds can delay the emergence of plants grown from seed, shorten stem height and delay flowering; these properties could be useful in preventing frost damage in countries where there is significant snow cover in the winter since then the treated plants would remain below snow cover during the cold weather. Further the compounds may cause drought or cold resistance in certain plants.

When applied as seed treatments at low rates the compounds can have a growth stimulating effect on plants.

It is to be understood that not all the compounds of the present invention will necessarily show all the above mentioned plant growth regulating effects. Thus whilst there may be advantages in compounds which have a broad spectrum of plant growth regulating effects against a wide range of species, compounds having a high specific activity with respect to a particular species and/or plant growth regulating effect may also be of great benefit.

In carrying out the plant growth regulating method of the invention, the amount of compound to be applied to regulate the growth of plants will depend upon a number of factors, for example the particular compound selected for use, and the identity of the plant species whose growth is to be regulated. However, in general an application rate of 0.1 to 15, preferably 0.1 to 5, kg per hectare is used. With the use of biodegradable polymeric slow release granules rates of 1 to 10 g per hectare are feasible; whilst electrodynamic spraying techniques may also deploy lower rates of application. However, on certain plants even application rates within these ranges may give undesired phytotoxic effects. Routine tests may be necessary to determine the best rate of application of a specific compound for any specific purpose for which it is suitable.

The compounds may also be active fungicide and may be used to control one or more of the following pathogens:

*Pyricularia cryzae* on rice.
*Puccinia recondita, Puccinia striiformis* and other rust on wheat, *Puccinia hordei, Puccinia striiformis* and other rusts on barley, and rusts on other hosts, e.g. coffee, pears, apples, peanuts, vegetables and ornamental plants.

*Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines.

*Helminthosporium* spp., *Rhynchosporium* spp., *Septoria* spp., *Pseudocercosporella herepotrichoides* and *Gaeumannomyces graminis* on cereals.

*Cercospora arachidicola* and *Cercosporidium personata* on peanuts and other Cercospora species on other hosts, for example, sugar beet, bananas, soya beans and rice.

*Botrytis cinerea* (grey mould) on tomatoes, strawberries, vegetables, vines and other hosts.

Alternaria species on vegetables (e.g. cucumber), oil seed rape, apples, tomatoes and other hosts.

*Venturia inaequalis* (scab) on apples.

*Plasmopara viticola* on vines.

Other downy mildews such as *Bremia lactucae* on lettuce, Peronospora spp. on soya beans, tobacco, onions and other hosts and *Pseudoperonospora humuli* on hops and *Pseudoperonospora cubensis* on cucurbits, *Phytophthora infestans* on potatoes and tomatoes and other Phytophthora spp. on vegetables, strawberries, avocado, pepper, ornamentals, tobacco, cocoa and other hosts.

*Thanaterphorus cucumeris* on rice and other Rhizoctonia species on various host such as wheat and barley, vegetables, cotton and turf.

Some of the compounds show a broad range of activities against fungi in vitro. They may also have activity against various post-harvest diseases on fruit (e.g. *Penicillium digitatum* and *Italicum* and *Trichoderma viride* on oranges, *Gloesporium musarum* on bananas and *Botrytis cinerea* on grapes.

Further some of the compounds may be active as seed dressings against Fusarium spp., Septoria spp., Tilletia spp., (bunt, a seed borne disease of wheat), Ustilago spp., Helminthosporium spp. on cereals, *Rhizoctonia solani* on cotton and *Pyricularia oryzae* on rice.

The compounds may be used as such for plant growth regulating purposes or as fungicides but are more conveniently formulated into compositions for such usage. The invention thus provides a plant growth regulating or fungicidal composition comprising a compound of general formula (I) as hereinbefore defined, or a salt or metal complex thereof; and, optionally, a carrier or diluent.

The invention also provides a method of regulating plant growth or of fungicidal treatment, which comprises applying to the plant, to seed of a plant or to the locus of a plant or seed, a compound, or a salt or metal complex thereof, as hereinbefore defined, or a composition combining the same.

The compounds, salts, metal complexes, ethers and esters can be applied in a number of ways, for example they can be applied, formulated or unformulated, directly to the foliage of a plant, or they can be applied also to bushes and trees, to seeds or to other medium in which plants, bushes or trees are growing or are to be planted, or they can be sprayed on, dusted on or applied as a cream or paste formulation, or they can be applied as a vapour; or as slow release granules Application can be to any part of the plant, bush or tree, for example to the foliage, stems, branches or roots, or to soil surrounding the roots, or to the seed before it is planted; or to the soil generally, to paddy water or to hydroponic culture systems. The invention compounds may also be injected into plants or trees and they may also be sprayed onto vegetation using electrodynamic spraying techniques.

The term "plant" as used herein includes seedlings, bushes and trees.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, kieselguhr, dolomite, calcium carbonate, talc, powdered magnesia, Fuller's earth, gypsum, Hewitt's earth, diatomaceous earth and China clay. Such granules can be preformed granules suitable for application to the soil without further treatement. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaohthalene, the xylenes, trichloroethylene, furfuryl alcohol, tetrahydrofurfuryl alcohol, and glycol ethers (e.g., 2-ethoxyethanol and 2-butoxyethanol).

The compositions to be used as sprays may also be in the form of aerosols wherein the formulation is held in a container under pressure in the presence of a propellant, e.g., fluorotrichloromethane or dichlorodifluoromethane.

The compounds can be mixed in the dry state with a pyrotechnic mixture to form a composition suitable for generating in enclosed spaces a smoke containing the compounds.

Alternatively, the compounds may be used in a microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The compounds can be used as mixtures with fertilisers (e.g., nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising the compound of general formula (I) or a salt or metal complex thereof.

The compositions may also be in the form of liquid preparations for use as dips or sprays which are generally aqueous dispersions or emulsions containing the active ingredient in the presence of one or more surfactants e.g., wetting agent(s), dispersing agent(s), emulsifying agent(s) or suspending agent(s); or which are spray formulations of the kind suitable for use in electrodynamic spraying techniques. The foregoing agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), and the concentrate is to be diluted with water before use. These concentrates often should be able to withstand storage for prolonged periods and after such storage be capable of dilution with water in order to form aqueous preparations which remain homogeneous for a sufficient time to enable them to be applied by conventional and electrodynamic spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylenesulphonic acid or dodecyl benzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% to 10%, or 0.01% to 10%, by weight of active ingredient(s) may be used.

The compositions of this invention can comprise also one or more additional compound(s) having biological activity, e.g., compounds having similar or complementary fungicidal or plant growth activity or compounds having plant growth regulating, herbicidal or insecticidal activity.

The additional fungicidal compound can be, for example, one which is capable of combating ear diseases of cereals (e.g., wheat) such as Septoria, Gibberella and Helminthosporium spp., seed and soil borne diseases and downy and powdery mildews on grapes and powdery mildew and scab on apple etc. Examples of suitable additional fungicidal compound are imazalil, benomyl, carbendazim, thiophanate-methyl, captafol, captan, sulphur, triforine, dodemorph, tridemorph, pyrazophos, furalaxyl, ethirimol, tecnazene, dimethirimol, bupirimate, chlorothalonil, vinclozolin, procymidone, iprodione, metalaxyl, forsetylaluminium, carboxin, oxycarboxin, fenarimol, nuarimol, fenfuram, methfuroxan, nitrotal-isopropyl, triadimefon, thiabendazole, etridiazole, triadimenol, biloxazol, dithianon, binapacryl, quinomethionate, guazatine, dodine fentin acetate, fentin hydroxide, dinocap, folpet, dichlofluanid, ditalimphos, kitazin, cycloheximide, dichlobutrazol, a dithiocarbamate, a copper compound, a mercury compound, 1-(2-cyano-2-methoxyiminoacetyl)-3-ethyl urea, fenaponil, ofurace, propiconazole, etaconazole and fenpropemorph and fenpropidine.

The compounds of general formula (I) can be mixed with soil, peat or other rooting media for the protection of plants against seed-borne, soil-borne or foliar fungal diseases.

Suitable additional insecticides are Pirimor, Croneton, dimeth- oate, Metasystox, pyrethroid insecticides and formothion.

The other, additional, plant growth regulating compound can be one which controls weeds or seedhead formation, improves the level or longevity of the plant growth regulating activity of the compounds of general formula (I), selectively controls the growth of the less desirable plants (e.g., grasses) or causes the compound of general formula (I) to act faster or slower as a plant growth regulating agent. Some of these other agents will also be herbicides.

Examples of suitable plant growth regulating compounds, which can display synergy in admixture, or use, with the invention compounds are the gibberellins (e.g., $GA_3$, $GA_4$ or $GA_7$), the auxins (e.g., indoleacetic acid, indolebutyric acid, naphthoxyacetic acid or naphthylacetic acid), the cytokinins (e.g., kinetin, diphenylurea, benzimidazole, benzyladenine or benzylaminopurine), phenoxyacetic acids (e.g., 2,4-D or MCPA), substituted benzoic acids (e.g., triiodobenzoic acid), morphactins (e.g., chlorfluorecol), maleic hydrazide, glyphosate, glyphosine, long chain fatty alcohols and acids, dikegulac, fluoridamid, mefluidide, substituted quaternary ammonium and phosphonium compounds (e.g., chlormequat* chlorphonium or mepiquat chloride*), ethephon, carbetamide, methyl-3,6-dichloroanisate, daminozide*, asulam, abscisic acid, isopyrimol, 1-(4-chlorophenyl)-4,6-dimethyl-2-oxo-1,2-dihydropyridine-3-carboxylic acid, hydrobenzonitriles (e.g., bromoxynil), difenzoquat*, benzoylprop-ethyl 3,6-dichloropicolinic acid, fenpentezol, triapenthanol, flurpirimidol, paclobutrazol, tetcyclacis and tecnazene. Synergy will be most likely to occur with those of the foregoing which are quaternary ammonium compounds and with those marked with an asterisk.

For certain applications, for example in the injection of the compounds of the invention into trees or plants, it is desirable that the compounds have a relatively high solubility in water, for example a solubility in excess of 30 parts per million. The compounds may alternatively be injected into the tree in the form of an organic solution, for example a solution in a lower alcohol.

For certain applications it is also desirable that the compound has a low persistancy in soil to prevent carry-over to adjacent crops or even crops planted subsequently in the same soil. Preferably the compound for use in such applications has a half life in the soil of less than 20 weeks.

The invention is illustrated by the following examples, in which Infra red characterisation of the compounds is given as $\gamma$ maximum (cm$^{-1}$); NMR characterisation of the compounds is given in terms of $\delta_H$; and mass sprectroscopy analysis is given in terms of m/z.

EXAMPLE 1

This Example illustrates the preparation of 1-phenyl-3-hydroxy-3-(pyrimidin-5-yl)-4-methylpent-1-yne (Compound No. 1 of Table I).

Stage 1

Preparation of 2-methyl-1-(pyrimid-5-yl)-propan-1-ol.

To a solution of n-butyl lithium (20 ml of 2.6 M, 52 mmol) in dry tetrahydrofuran (60 ml) at −78° C., was added a cold solution of 5-bromopyrimidine (6.36 g, 40 mmol) in dry tetrahydrofuran (30 ml) over a period of 5 minutes. After 10 minutes a cold solution of isobutyraldehyde (2.88 g, 40 mmol) in dry tetrahydrofuran (30 ml) was added dropwise. The mixture was allowed to warm to room temperature and stirred for 16 hours. The reaction mixture was poured into water and extracted with ether (2×100 ml). The organic layer was collected, washed with brine and dried over magnesium sulphate before removing the solvent. Flash chromatography (silica gel, petrol/ether elution) gave the product as a yellow oil.

Stage 2

Preparation of 2-methyl-1-(pyrimid-5-yl)-propan-1-one.

To a suspension of chromium (VI) oxide (12.87 g, 65 mmol) in dry dichloromethane (500 ml) was added dry pyridine (10.27 g, 130 mmol) and the mixture stirred for 0 5 h. Then a solution of 2-methyl-1-(pyrimid-5-yl)-propan-1-ol, prepared in stage 1, (1.52 g, 10 mmol) in dry dichloromethane (100 ml) was added dropwise with stirring. After 2 hours the reaction mixture was poured into ether (1000 ml) and then filtered. The filtrate was washed with copper sulphate solution (4×400 ml), brine solution (2×400 ml), and dried over magnesium sulphate before removing the solvent. Flash chromatography (silica gel, petrol/ether elution) gave the product as a colourless oil (0.72 g, 48%).

Stage 3

To a solution of phenyl acetylene (1.36g, 13.3 mmol) in dry tetrahydrofuran (40 ml) at −78° C. was added n-butyl lithium (13.3 mmol). After 15 minutes, chlorotitanium triisopropoxide (13.3 mmol) was added and the reaction stirred for 30 minutes. To this mixture was added 2-methyl-1-(pyrimid-5-yl)-propan-1-one (2.0g, 13.3 mmol) as a solution in dry tetrahydrofuran (20 ml), and the mixture was allowed to warm to room temperature. The reaction mixture was stirred for 16 hours and then poured into water. The titanium residues were filtered off and washed with ether (2×200 ml). The combined ether extracts were washed with saturated brine, dried over magnesium sulphate and the solvent was removed. Flash chromatography (silica gel, petrol/ether elution) gave the product as a white solid (1 48g) having a melting point of 112°-113° C.

The product was further characterised as follows:
Infra red: 3150, 2220, 1560, 1410, 1260, 1130, 1040, 980, 950, 920, 870, 760, 740, 690, cm$^{-1}$.

NMR (250 MHz; CDCl$_3$): 0.89 (3H, d, J=7.2 Hz), 1.09 (3H, d, J=7.2 Hz), 2.11 (1H, sept, J=7.2 Hz), 4.32 (1H, s), 7.3 (3H, m), 7.4 m), 8.94 (2H, s), 9.1 (1H, s).

EXAMPLE 2

Compound No. 2 of Table I was prepared by reduction of Compound No 1, prepared as in Example 1 above. To a solution of Compound No. 1 (1.1 g, 4 mmol) in ethanol (80 ml) was added palladium on charcoal (1 g of 5%). The reaction vessel was pressurised with hydrogen (200 psi) at ambient temperature and agitated. The reaction was followed by gas-liquid chromatography and was found to be complete after 24 hours. The catalyst was filtered off and the solvent removed. The organic phase was collected, washed with water and brine, dried over magnesium sulphate and the solvent removed. The resulting residue was purified by flash chromatography over silica gel with petrol/diethyl ether solution to give the product as a colourless gum which was characterised as follows:

Infra red: 3350, 2975, 1570, 1410, 1170, 1030, 920, 740, 710, 640 cm$^{1-}$.

NMR (90 MHz; CDCl$_3$): 0 80 (3H, d, J=7.2 Hz), 1.0 (3H, d, J=7 2 Hz), 1.90–2.80 (6H, m), 7.0–7.4 (5H, m), 8.8 (2H, s), 9.1 (1H, s).

EXAMPLE 3

This Example illustrates the preparation of 1-phenyl-3-hydroxy-3-(pyrimidin-5-yl)-4,4-dimethylpent-1-yne (Compound No. 3 of Table I).

Compound No. 3 was prepared using the general method of Example 1 by reacting phenylacetylene (1.36 g, 13.3mmol), n-butyl lithium (5.32 ml of 2.5M, 13.3mmol), chlorotitanium tri-isopropoxide (13.3mmol of 1M, 13.3mmol) and 2,2-dimethyl-1-(pyrmid-5-yl)-propan-1-one. The 2,2-dimethyl-1-(pyrmid-5-yl)-propan-1-one intermediate was prepared by reaction of 5-bromopyrimidine with 2,2-dimethylpropanealdehyde and subsequent oxidation of the product, using the general method of stages 1 and 2 of Example 1.

The product was yellow solid having a melting point of 118° C. and further characterised by its NMR spectrum as follows:

NMP (250 MHz; CDCl$_3$): 1.03 (9H, s), 3.8 (1H, s), 7.3–7.5 (5H, m), 8.99 (2H, s), 9.08 (1H, s).

EXAMPLE 4

Compound No. 4 of Table I was prepared by reduction of Compound No. 3, prepared as in Example 3 above. To a solution of Compound No. 3 (1.0 g, 3.9 mmol) in ethanol (80ml) was added palladium on charcoal (lg of 5%). The reaction vessel was pressurised with hydrogen (200 psi) at ambient temperature and agitated. The reaction was followed by gas liquid chromatography and was found to be complete after 24 hours. The catalyst was filtered off and the solvent removed. The organic phase was collected, washed with water and brine, dried over magnesium sulphate and the solvent removed. The resulting residue was purified by flash chromatography over silica gel with petrol/diethyl ether elution to give the product as a white solid of melting point 95°-97° C., which was further characterised as follows:

NMR (90 MHz; CDCl$_3$): 0.94 (9H, s), 1.22 (1H, s), 2.1–2.6 (4H, m), 7.0–7.2 (5H, m), 8.78 (2H, s), 9.06 (1H, s).

EXAMPLE 5

This Example illustrates the preparation of 1(4'-chlorophenyl)-3-hydroxy-4-methyl-3-(pyrimidin-5-yl)-pent-1-yne (Compound No. 5 of Table I).

Stage 1

Preparation of 2(4'-chlorophenyl)-1-trimethylsilylethyne. To a solution of 4-chloroiodobenzene (4.77 g:0.02 mole) in dry acetonitrile (30 ml) and triethylamine (2.02 g:0.02 mole) under nitrogen, was added copper iodide (0.2 g:1.05 mole), bis (triphenylphosphine)palladium dichloride (0.2 g=0.285 mmole) and trimethylsilylethyne (2.156 g:0.022 mole). The mixture was stirred for three hours during which time there was an exotherm at 20° C. and a darkening of the reacton mixture. The mixture was poured into saturated ammonium chloride solution (100 ml) and was extracted with ether (×3). The extracts were combined, washed with dilute hydrochloric acid and dried over magnesium sulfate and then filtered through charcoal. Removal of solvent in vacuo gave a brown oil which was titurated with hexane and filtered to remove by-products. The filtrate was evaporated to give yellow crystals (3.90 g).

Stage 2

Preparation of 1(4'-chlorophenyl)ethyne. To a solution of 2(4-chlorophenyl)-1-trimethylsilylethyne Prepared in Stage 1 (30.90g:0.02 mole) in methanol was added potassium carbonate (0.276g:002 mole). The mixture was stirred at room temperature until starting material disappeared as monitored by gas liquid chromatography. After this time, solvent was removed in vacuo and the residue taken up in dichloromethane. The solution was dried and declourised over charcoal. Filtration, followed by removal of solvent gave a brown solid which was passed through silica in hexane. This gave pale yellow crystals (1.511g:55.3%)

Stage 3

Preparation of 1(4'-chlorophenyl)-3-hydroxy-4-methyl-3-(pyrimidin-5-yl)-pent-1-yne.

1(4'-Chlorophenyl)ethyne (1.43g:0.01 mole) was dissolved in tetrahydrofuran (10 ml) under nitrogen and cooled to −35° C. Butyllithium was added (6.5 ml of 1.6M solution:0.0104 mole) causing the colour to change. The mixture was stirred for ½ hour during which time it thickened and the colour changed to pink (from purple). Addition of a solution of chlorotanium triisopropoxide (10.6 ml or a 1 molar solution:0.0106 mole) caused the colour to change to yellow and the mixture was stirred for 20 minutes. The mixture was cooled to −60° C. and a solution of 2-methyl 1(pyrimidin-5-yl)propan-1-one in tetrahydrofuran (10 ml) was added and the reaction mixture allowed to warm up to room temperature within the cold bath. A solution of ammonium chloride in water (20%) was added and the mixture filtered. The aqueous was extracted with ethyl acetate (×3), washed (with water then brine), dried and the solvent removed in vacuo. The product was passed through silica (in ether) and then titurated with pentane and ether (0.467g: off white solid).

$^1$H NMR (270 MHz, CDCl$_3$): 0.94 (3H, d); 1.10 (3H, d); 2.18 (multiplet 1H); 3.60 (1H, s); 7.35 (4H, m); 8.9 (2H, s); 9.15 (1H, s).

EXAMPLE 6

This Example illustrate the preparation of 1-(4-chlorophenyl)-3-hydroxy-4,4'-dimethyl-3-(pyrimidin-5-yl)pentane (Compound No. 6 of Table I).

In dry apparatus under nitrogen, n-butyllithium (7.9 mls of 2.4M in hexane, 0.019 mols) was added to dry diethylether and tetrahydrofuran (20 mls, 1:1) at −95° C. A solution of 5-bromopyrimidine (3.0 g, 0.019 mols) in dry ether and tetrahydrofuran (20 ml, 1:1) was gradually added dropwise with stirring, keeping temperature below −80° C. The yellow suspension was stirred at −95° C. for ½ hour, then a solution of t-butyl-4-chlorophenethylketone (4.24g, 0.019 mols) in dry diethyl ether and tetrahydrofuran (10 ml, 1:1) was gradually added dropwise, keeping the temperature below −80° C. The reaction mixture was allowed to reach 20° C. overnight and then hydrolysed with water. More ether was added and organics were separated. The aqueous layer was re-extracted with ether and the combined organics were washed with brine, dried and concentrated in vacuo to give a suspended solid. Tituration with pentane followed by filtration gave the product as a white solid (1.36 g) having melting point 154°–156° C.

EXAMPLES 7 AND 8

Compound Nos. 7 and 8 of Table I were prepared using the general method of Example 6 and were solids characterised by the melting point given in Table I.

EXAMPLES 9 TO 11

Compound Nos. 9 to 11 and compounds 18 and 19 of Table I were prepared using the general method of Example 5 and were solids characterised by the melting point given in Table I.

EXAMPLE 12

Preparation of 1-(2,4-dichlorophenyl)-3-hydroxy-4-methyl-3-(pyrimidin-5-yl)pent-1-ene (Compound No. 12).

Stage 1

2,4-Dichlorobenzaldehyde (10.0 g, 0.057 mols) and isopropylmethylketone (4.92g, 0.057 mols) were dissolved in ethanol and water (50 ml, 4:1) at 20° C. Aqueous sodium hydroxide (5.7 mls of 10%, 0.014 mols) was added with stirring. After 3 hours at 20° C., a suspension resulted. After standing overnight dichloromethane was added. The solution was extracted with water then brine. The dichloromethane layer was dried and concentrated in vacuo to leave an orange oil which crystallised on standing overnight. The solid was triturated with pentane and filtered to give a cream solid (6.39 g).

Melting point: 56°–59° C.

Stage 2

In dry apparatus under nitrogen, n-butyllithium (13.6 ml of 1.6 molar in hexanes, 0.022 mols) was dissolved in dry tetrahydrofuran and dry diethylether (80ml, 1:1) at −80° C. A solution of 5-bromopyrimidine (3.46 g, 0.022 mols) in tetrahydrofuran and ether (30 ml, 1:1) was gradually added dropwise with stirring at −95° C. Stirred at −95° C. for 15 minutes, then a solution of the product of Stage 1 (5.285 g, 0.022 mols) in tetrahydrofuran and ether (20 ml, 1:1) was gradually added with stirring at −95° C. The suspension was allowed to reach 20° C. overnight and then hydrolysed with water. The organic layer was separated. The aqueous layer was re-extracted with ether (×2) and the combined ether extracts were washed with water then brine. The extracts were dried and concentrated in vacuo. The orange oil then produced crystallised on trituration with ether/pentane to give the desired product as a pale cream solid. The residues from filtration were further purified by chromatography using silica and ether:hexane (1:1) as eluent. This gave a further 0.49 g of product.

Melting point: 111°–113° C.

EXAMPLES 13 TO 17

The procedure of Example 12 was used to prepare Compound Nos. 13 to 17. All except Compound No. 14 were solids characterised by their melting Point as given in Table I. Compound No. 14 was an oil characterised by its NMR spectrum:

1-(2-methoxyphenyl)-3-hydroxy-4-methyl-3-(pyridin-5-yl)-pent-1-ene.

NMR (CDCl$_3$) H:0.88 (3H, d), 1.00 (3H, d), 2.17–2.32 (1H, mult); 3.81 (3H, s); 3.97 (1H, s); 6.65 (1H, d); 6.85–7.0 (2H, m); 7.10 (1H, d); 7.2–7.5 (2H, m); 8.92 (2H, s); 9.09 (1H, s).

EXAMPLE 18

Compound Nos. 1 to 4 in Table I were tested for plant growth regulator activity against six species for various growth effects relevant to plant growth regulation.

Methodology

The plant species used in this screen are presented in Table II with the leaf stage at which they were sprayed. Each chemical was applied at 4000 ppm (4 kg/ha in a 1000 l/ha field volume) using a tracksprayer and a SS8004E (Teejet) nozzle.

After spray the plants were grown in a glasshouse with 25° C. day/22° C. night temperatures and supplementary lighting was supplied when necessary (from mercury vapour lamps), to provide a 16 hour photoperiod. The exception to this were the temperate cereals, wheat and barley which were grown in 16° C. day/13° C. night temperatures.

After 2–6 weeks in the glasshouse, depending on the time of year, the plants were visually assessed for morphological characteristics. Formulation blanks were used as controls to assess the plants. The results are presented in Tables III, IV and V.

TABLE II

| PLANT MATERIAL USED FOR WHOLE PLANT SCREEN | | | | |
|---|---|---|---|---|
| Species | Code | Variety | Growth Stage at Treatment | No. Plants per 3" Pot | Compost Type |
| Barley | BR | Atem | 1–1.5 leaves | 4 | JIP* |
| Wheat | WW | Timmo | 1–1.5 leaves | 4 | JIP |
| Maize | MZ | Earliking | 2¼ leaves | 1 | PEAT |
| Apple | AP | Red Delicious | 4–5 leaves | 1 | JIP |
| Rice | RC | Ishikari | 2–2½ leaves | 4 | JIP |
| Tomato | TO | Ailsa Craig | 2–2½ leaves | 1 | JIP |

JIP* = John Innes Potting Compost.

TABLE III

| COMPOUND NO. | BR | | | | | WW | | | | |
|---|---|---|---|---|---|---|---|---|---|---|
| | R | G | A | T | I | R | G | A | T | I |
| 1 | 3 | 2 | | 3 | 3 | 2 | 2 | | 3 | 3 |
| 2 | 2 | 1 | | 2 | 3 | 3 | 2 | | 3 | 3 |
| 3* | 3 | 2 | | 3 | 3 | 1 | 1 | | 2 | 1 |
| 4 | 3 | 3 | | | 3 | 3 | 1 | | 2 | 3 |
| 5 | 2 | | | | 2 | 3 | 1 | | 1 | 3 |
| 6 | 2 | | | | 2 | 3 | 2 | | | 3 |
| 7 | | | | | | 3 | 2 | | | 3 |
| 8 | | | | | | 2 | 1 | | 2 | 2 |
| 9* | | | 1 | | | 1 | 1 | | | 1 |
| 10 | 3 | 1 | | | 3 | 2 | 1 | | | 3 |
| 11 | 2 | 1 | | 1 | 2 | 3 | 1 | | | 3 |
| 12 | 1 | | | 1 | 1 | 2 | | | 1 | 2 |
| 13 | 3 | 2 | | 3 | 3 | 3 | 1 | | 1 | 3 |
| 14 | | | | 1 | | 1 | | | | 1 |
| 15 | 2 | 2 | | 3 | 2 | 3 | 1 | | 1 | 3 |
| 16 | 2 | 2 | | | 2 | 2 | 1 | | | 2 |
| 17 | 2 | 2 | | 2 | 2 | 3 | 1 | | | 3 |

*Applied at 1 kg/ha

TABLE VI

| COMPOUND NO. | RC | | | | | AP | | | | |
|---|---|---|---|---|---|---|---|---|---|---|
| | R | G | A | T | I | R | G | A | T | I |
| 1 | 3 | 1 | | | 3 | 3 | 1 | | | 3 |
| 2 | 2 | 1 | | | 2 | 3 | 2 | | | 3 |
| 3 | — | — | — | — | — | — | — | — | — | — |
| 4 | — | — | — | — | — | — | — | — | — | — |

TABLE V

| COMPOUND NO. | TO | | | | |
|---|---|---|---|---|---|
| | R | G | A | T | I |
| 1 | | 1 | | | |
| 2 | 2 | 2 | | | 2 |
| 3* | 2 | 2 | | | 2 |
| 4 | 3 | 3 | | | 3 |
| 5 | 2 | 2 | | | 2 |
| 6 | 3 | 2 | | | 3 |
| 7 | 3 | 1 | | | 3 |
| 8 | 3 | 1 | | | 3 |
| 9* | | | | | |
| 10 | | | | | |
| 11 | 1 | | | | 1 |
| 12 | 3 | 2 | | 2 | 3 |
| 13 | 2 | 1 | | | 2 |
| 14 | | | | | |
| 15 | | 1 | | | |
| 16 | | | | | |
| 17 | 3 | 2 | | 2 | 3 |

*Applied at 1 kg/ha

Key:
R = Retardation
G = Greening effect
A = Apical damage
T = Tillering or side shooting
I = Interligular or internodal length reduction
All effects are scored visually on a 1–3 basis where
1 = 10–30%
2 = 31–60%
3 = 61–100%

EXAMPLE 19

Intermediate Retardant Test

Methodology

Three species are involved in Test (a) RICE, SPRINGBARLEY and APPLES. In Test (b) sunflower was added whilst in Test (c) brassica napus was added. The variety and growth stages at spray are outlined in Table VI. Compounds were applied at 500 ppm or 2000 ppm (0.5 kg and 2 kg ha$^{-1}$ at a field volume of 1000 l ha$^{-1}$) as an overall spray except where indicated. This gives a foliar and root component in the test, i.e., this test will detect the activity of both root and foliar acting compounds. Otherwise a foliar (only) spray at 2000 ppm was compared with a root drench, also at 2000 ppm. The rice was grown in 4 'paddy' pots, i.e., the roots and bottom of the stems are immersed in water under conditions corresponding to those in paddy fields. Spring barley and apples were grown in 4 pots. The plants were assessed for height to top-most ligule at approximately 28 days after treatment for spring barley and rice and for height to apex at approximately 28 days after the treatment for apples. The results are presented in Tables VI to X. In each case the result for the 2000 ppm (or 500 ppm) test for each compound is compared to the height of the formulation blank in that test, presented as a percentage reduction in height compared to the formulation blank. A blank indicates that the compound was substantially inactive as a retardant at that particular rate of application.

TABLE IX

Percentage Reduction in Height of Apples.
(Compared to formulation blank).

| COMPOUND NO | Rate | |
|---|---|---|
| | 2000 ppm (Foliar) | 2000 ppm (Root) |
| 1 | 46 | 63 |

TABLE X

Percentage Reduction
(Compared to formulation blank)
SPECIES AND MODE OF APPLICATION

| COMPOUND NO. | Barley (overall spray) | Rice (overall spray) | Apples (overall spray) | Sunflower (Foliar) | Sunflower (root) | Brassica napus (foliar) | Brassica napus (root) | Apples (foliar) |
|---|---|---|---|---|---|---|---|---|
| 3 | 62 | 43 | 68 | — | 19 | — | — | — |
| 4 | 44 | 57 | 67 | — | 29 | — | — | — |
| 5 | 67 | 43 | 73 | — | — | 49 | 68 | — |
| 6 | 64 | 27 | 68 | — | — | 69 | 77 | — |
| 7 | 30 | 28 | 73 | — | — | 39 | 67 | |
| 8 | 40 | 9 | 74 | — | — | 78 | 49 | — |
| 10 | 49 | 36 | — | — | — | 8 | 25 | 2 |
| 11 | 36 | 38 | — | — | — | 17 | 46 | 33 |

All compounds applied at 2000 ppm

TABLE VI

PLANT MATERIAL FOR INTERMEDIATE RETARDANT TEST

| Species | Variety | Growth Stage at Treatment | No Plants per 4" Pot | Compost Type |
|---|---|---|---|---|
| Spring Barley | Atem | 3 leaves | 4 | JIP 1 |
| Rice | Ishikari | 3-4 leaves | 2 | SM2:JIP 1 |
| Apples | Red Delicious | 5-10 cm high | 1 | SM2:JIP 1 |
| Sunflower | Elia | 2-3 leaves | 1 | JIP 1 |
| Brassica napus | Rapid Cycling | 3-4 leaves or early bud formulation | 1 | JIP 1 |

JIP 1 = John Innes Potting Compost.
SM2 = a mixture of loam and grit.

TABLE VII

Percentage Reduction in Height of Rice.
(Compared to formulation blank).

| COMPOUND NO | Rate | |
|---|---|---|
| | 500 ppm | 2000 ppm |
| 1 | 16 | 48 |

TABLE VIII

Percentage Reduction in Height of Spring Barley.
(Compared to formulation blank).

| COMPOUND NO | Rate | |
|---|---|---|
| | 500 ppm | 2000 ppm |
| 1 | 39 | 63 |

EXAMPLE 20

The compounds were tested against a variety of foliar fungal diseases of plants. The technique employed was as follows.

The plants were grown in John Innes Potting Compost (No. 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredients) were sprayed onto the foliage and applied to the roots of the plants in the soil. The sprays were applied to maximum retention and the root drenches to a final concentration equivalent to approximately 40 ppm a.i./dry soil. Tween 20, to give a final concentraton of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading :
4 = no disease
3 = trace −5% of disease on untreated plants
2 = 6–25% of disease on untreated plants
1 = 26–59% of disease on untreated plants
0 = 60–100% of disease on untreated plants The results are shown in Table XI.

TABLE XI

| COMPOUND NO. (TABLE I) | PUCCINIA RECONDITA (WHEAT) | ERYSIPHE GRAMINIS (BARLEY) | VENTURIA INAEQUALIS (APPLE) | PYRICULARIA ORYZAE (RICE) | CERCOSPORA ARACHIDICOLA (PEANUT) |
|---|---|---|---|---|---|
| 3 | 4 | 4 | 4 | 2 | 4 |
| 4 | 4 | 4 | 4 | 3 | 4 |
| 5 | 0 | 4 | 0 | 3 | 4 |
| 6 | 4 | 4 | 4 | 1 | 4 |
| 7 | 3 | 4 | 4 | 2 | 4 |
| 8 | 4 | 3 | 3 | 1 | 4 |
| 9 | 0 | 2 | 0 | 0 | 0 |
| 10 | 0 | 4 | 4 | 0 | 0 |
| 11 | 0 | 3 | 0 | 0 | 0 |
| 12* | 0 | 4 | 0 | 0 | — |
| 14* | 0 | 4 | 0 | 0 | — |
| 15* | 3 | 4 | 0 | 4 | — |
| 16* | 3 | 4 | 0 | 4 | — |
| 17* | 3 | 4 | 0 | 4 | — |

*Applied at 50 ppm active ingredient

The manner in which the compounds of the present invention may be formulated into compositions suitable for application is shown generally in the following indicative illustrations numbered as Examples 21 to 30.

EXAMPLE 21

An emulsifiable concentrate is made up by mixing the following ingredients, and stirring the mixture until all the constituents were dissolved.

| Compound of Table I | 10% |
|---|---|
| Calcium dodecylbenzensulphate | 5% |
| "SYNPERONIC" NP13 | 5% |
| "Aromasol" H | 80% |

EXAMPLE 22

A composition in the form of grains readily dispersible in a liquid, e.g. water, is prepared by grinding together the first three ingredients in the presence of added water and then mixing in the sodium acetate. The resultant mixture is dried and passed through a British Standard mesh sieve, size 44–100, to obtain the desired size of grains.

| Compound of Table I | 50% |
|---|---|
| "Dispersol" T | 25% |
| "SYNPERONIC" NP5 | 1.5% |
| Sodium acetate | 23.5% |

EXAMPLE 23

The following ingredients are ground together to produce a powder formulation readily dispersible in liquids.

| Compound of Table I | 45% |
|---|---|
| "Dispersol" T | 5% |
| "SYNPERONIC" NX | 0.5% |
| "Cellofas" B600 | 2% |
| China clay GTY powder | 47.5% |

EXAMPLE 24

The active agent is dissolved in acetone and the resultant liquid is sprayed on to the granules of attapulgite clay. The solvent is then allowed to evaporate to produce a granular composition.

| Compound of Table I | 5% |
|---|---|
| Attapulgite granules | 95% |

EXAMPLE 25

A composition suitable for use as a seed dressing is prepared by mixing the three ingredients.

| Compound of Table I | 50% |
|---|---|
| Mineral oil | 2% |
| China clay | 48% |

EXAMPLE 26

A dusting powder is prepared by mixing the active ingredient with talc.

| Compound of Table I | 5% |
|---|---|
| Talc | 95% |

EXAMPLE 27

A flowable formulation is prepared by bead-milling the constituents set out below and then forming an aqueous suspension of the ground mixture with water.

| Compound of Table I | 40% |
|---|---|
| "Dispersol" T | 4% |
| "SYNPERONIC" NP5 | 1% |
| Water | 55% |

EXAMPLE 28

A dispersible powder formulation is made by mixing together the ingredients set out below and then grinding the mixture until all were thoroughly mixed.

| Compound of Table I | 25% |
|---|---|
| "Aerosol" OT/B | 2% |
| "Dispersol" A.C. | 5% |
| China clay | 28% |
| Silica | 40% |

EXAMPLE 29

This example illustrates the preparation of a dispersible powder formulation. The ingredients are mixed and the mixture then ground in a comminution mill.

| Compound of Table I | 25% |
| --- | --- |
| "PERMINAL" BX | 1% |
| "Dispersol" T | 5% |
| Polyvinylpyrrolidone | 10% |
| Silica | 25% |
| China clay | 34% |

EXAMPLE 30

The ingredients set out below are formulated into dispersible powder by mixing then grinding the ingredients.

| Compound of Table I | 25% |
| --- | --- |
| "Aerosol" OT/B | 2% |
| "Dispersol" A | 5% |
| China clay | 68% |

In Examples 7 to 16 proportions of the ingredients given are by weight.

There now follows an explanation of the compositions or substances represented by the various Trade Marks and Trade Names mentioned above.

| "SYNPERONIC" NP13: | a condensate of nonyl phenol (1 mole) with ethylene oxide (13 moles). |
| --- | --- |
| "AROMASOL" H: | a solvent mixture of alkylbenzenes. |
| "DISPERSOL" T AND AC: | a mixture of sodium sulphate and a condensate of formaldehyde with sodium naphthalene sulphonate. |
| "SYNPERONIC" NP5 | a condensate of nonyl phenol (1 mole) with naphthalene oxide (5.5 moles). |
| CELLOFAS B600: | a sodium carboxymethyl cellulose thickener. |

We claim:

1. A pyrimidine derivative having the general formula (I):

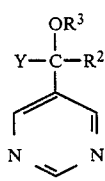   (I)

and stereoisomers thereof, wherein Y is optionally substituted cyclopropyl or optionally substituted 1-methylcyclopropyl or is the group:

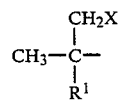   (II)

wherein $R^1$ is hydrogen or methyl; X is hydrogen or halogen; $R^2$ is a group:

$$-(CH_2)_m-C\equiv C-A \quad (III)$$

or $$-(CH_2)_n-CH=CH-A \quad (IV)$$

or $$-(CH_2)_p-A \quad (V)$$

wherein A is an optionally substituted phenyl group, m is an integer from 0 to 2, n is an integer from 0 to 2 and p is an integer from 2 to 4; and $R^3$ is hydrogen, an alkyl group containing from 1 to 4 carbon atoms, an alkenyl group containing from 3 to 4 carbon atoms or an alkynyl group containing from 3 to 4 carbon atoms and agrochemically acceptable salts, esters and metal complexes of the compounds of formula (I) wherein $R^3$ is hydrogen.

2. A pyrimidine derivative according to claim 1 wherein the integers n and m are 0 and the integer p is 2.

3. A pyrimidine derivative according to claim 2 wherein Y is the group

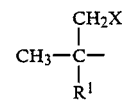

$R^2$ is the group $-C\equiv C-A$, and $R^3$ is hydrogen or an alkyl group containing from 1 to 4 carbon atoms.

4. A pyrimidine derivative according to claim 1 wherein, in the group Y in formula (I), the group X is hydrogen, chlorine or fluorine or the optional substituent which may be present in the cyclopropyl or 1-methylcyclopropyl group is chlorine or fluorine.

5. A pyrimidine derivative according to claim 1 wherein A is unsubstituted phenyl or is phenyl substituted with one or more substituents selected from halogen, alkyl containing from 1 to 6 carbon atoms, cycloalkyl containing from 3 to 6 carbon atoms, alkoxy containing from 1 to 6 carbon atoms, haloalkyl containing from 1 to 6 carbon atoms, nitro and cyano.

6. A pyrimidine derivative according to claim 1 wherein $R^3$ is hydrogen or methyl.

7. A plant growth regulating composition comprising a plant growth regulating amount of a pyrimidine derivative according to claim 1 and an agrochemically acceptable carrier or diluent.

8. A method of regulating plant growth which comprises applying to the plant, to the seed of the plant, or to the locus of the plant or seed of a plant growth regulating amount of a pyrimidine derivative according to claim 1.

9. A fungicidal composition comprising a fungicidally effective amount of a pyrimidine derivative according to claim 1 and an agrochemically acceptable carrier or diluent.

* * * * *